United States Patent [19]

Krishnan et al.

[11] 4,446,297

[45] May 1, 1984

[54] THERMOPLASTIC COPOLYCARBONATE FROM HALOGEN FREE AROMATIC DIOL AND HALOGENATED THIODIPHENOL

[75] Inventors: Sivaram Krishnan, Moers, Fed. Rep. of Germany; Arthur L. Baron, New Martinsville, W. Va.

[73] Assignee: Mobay Chemical Corporation, Pittsburgh, Pa.

[21] Appl. No.: 366,453

[22] Filed: Apr. 7, 1982

Related U.S. Application Data

[60] Division of Ser. No. 232,470, Feb. 9, 1981, abandoned, which is a continuation-in-part of Ser. No. 110,273, Jan. 7, 1980, abandoned.

[30] Foreign Application Priority Data

Dec. 26, 1980 [JP] Japan ............................. 55-184165

[51] Int. Cl.$^3$ ............................................. C08G 63/62
[52] U.S. Cl. .................................... 528/204; 528/171; 528/196
[58] Field of Search ..................... 528/204, 196, 171

[56] References Cited

U.S. PATENT DOCUMENTS

| | | | |
|---|---|---|---|
| 2,695,317 | 11/1954 | Cutler | 260/609 |
| 3,023,101 | 2/1962 | Ossenbrunner et al. | 96/87 |
| 3,250,744 | 5/1966 | Schnell et al. | 260/47 |
| 3,332,960 | 7/1967 | Werner | 260/309.6 |
| 3,437,631 | 4/1969 | Cleveland | 260/37 |
| 3,912,687 | 10/1975 | Haupt et al. | 260/47 XA |
| 4,043,980 | 8/1977 | Baron et al. | 260/47 XA |
| 4,075,119 | 2/1978 | Schmidt et al. | 252/182 |
| 4,170,587 | 10/1979 | Schmidt et al. | 260/37 PC |
| 4,174,359 | 11/1979 | Sivaramakrishnan et al. | 525/1 |
| 4,282,391 | 8/1981 | Quinn et al. | 568/726 |

FOREIGN PATENT DOCUMENTS 50-6785075  6/1975  Japan.

OTHER PUBLICATIONS

Hay-cols. 1-2, 35-36, USP 3,306,875.
Mark et al.—Physical Chemistry of High Polymeric Systems, 1950, pp. 274-275.
Japanese Abstract A-51-149351.

*Primary Examiner*—Harold D. Anderson
*Attorney, Agent, or Firm*—Gene Harsh; Lawrence S. Pope; Aron Preis

[57] ABSTRACT

Polycarbonates are provided having improved critical thickness values and flame retardant characteristics based upon an aromatic diol and a halogenated thiodiphenol represented by the structural formula

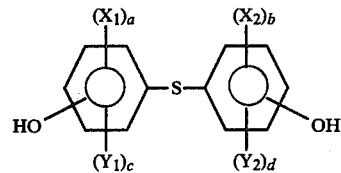

wherein $X_1$ and $X_2$ are halogen and "a"+"b"=1 to 8; $Y_1$ and $Y_2$ are alkyl groups having 1 to 4 carbon atoms; and "c"+"d"=0 to 7. By incorporating an effective amount of the aromatic halogenated thiodiphenol, based upon the total aromatic diol content, into the polymer the critical thickness and flame retardant characteristics of the polycarbonate are substantially improved, a process for the preparation of the monomer of said structural formula is likewise provided.

11 Claims, No Drawings

THERMOPLASTIC COPOLYCARBONATE FROM HALOGEN FREE AROMATIC DIOL AND HALOGENATED THIODIPHENOL

This application is a division of application Ser. No. 232,470, filed Feb. 9, 1981, now abandoned which itself is a continuation-in-part of Ser. No. 110,273 filed Jan. 7, 1980, now abandoned.

BACKGROUND OF THE INVENTION

1. Field of the Invention

This invention relates to polycarbonate resins and more particularly to flame retardant polycarbonate copolymers having improved critical thickness values.

2. Description of the Prior Art

Polycarbonates derives from reactions involving organic dihydroxy compounds and carbonic acid derivatives have found extensive commercial application because of their excellent mechanical and physical properties. These thermoplastic polymers are particularly suited for the manufacture of molded article products requiring impact strength, rigidity, toughness, thermal and dimensional stability as well as excellent electrical properties.

However, one deficiency of polycarbonate when used in molded articles is the low critical thickness values of polycarbonate polymer, which deficiency tends to limit wall thickness to a value below the critical thickness.

It is known that polycarbonate plastics exhibit high notched Izod (ASTM test D-256) impact values. This value, however, is dependent upon the thickness of the test specimen. Typical notched Izod impact values for a ⅛" specimen are about 16 ft.-lbs./in. These high Izod values result because specimens of ⅛" thickness are thinner than the critical thickness of the polymer and therefore upon impact a hinged or ductile break occurs. On the other hand, ¼" specimens exhibit a clean or brittle break and give notched Izod impact values of only about 2.5 ft.-lbs./in. The ¼" specimens are said to be above the critical thickness of the polymer. "Critical thickness" has been defined as the thickness at which a discontinuity in Izod impact values occur. In other words, it is the thickness at which a transition from a brittle to a ductile break or vice versa occurs. Thus a standard impact specimen of polycarbonate polymer thicker than the critical thickness exhibits brittle breaks and those thinner than the critical thickness exhibit hinged or ductile breaks. Further, the critical thickness of a polycarbonate based on bisphenol A with a melt flow of 3 to 6 grams/10 minutes at 300° C. (ASTM D1238) has a critical thickness of about 225 mils.

The critical thickness problem is further complicated when the polycarbonate article is to meet a specified requirement for flammability in applications where high temperature and/or exposure to fire may be encountered. Polycarbonate copolymers based on an aromatic diol and a halogenated diol reacted with a carbonic acid derivative are accepted as effective fire retardant polymers. These polymers exhibit generally acceptable physical properties along with complying with flammability requirements. However, the critical thickness of copolymers employing halogenated diols is very low for example about 130-140 mils with a polymer containing 5 to 6% by weight bromine in the form of a halogenated diol.

One approach to solving the critical thickness problem has been to incorporate polyolefin polymers into the polycarbonate which has substantially improved critical thickness (see U.S. Pat. No. 3,437,631). But along with this improvement has come detrimental effects such as colorant dispersion problems because of the diversity of chemical composition of the two component system and also a lack of transparency since the polyolefin and the polycarbonate are incompatible.

Improvement in critical thickness of polycarbonates has been accomplished by incorporating amounts of a sulfur containing aromatic diol into the polymer chains. This has been effective in both flame retardant and non-flame retardant polycarbonates. Further, it has been found that the sulfur in the sulfur containing aromatic diol provides a synergistic effect with the halogen moieties of a second aromatic diol providing a more flame retardant product. Exemplary of the advantages of incorporating sulfur containing aromatic diols, particularly thiodiphenol type diols, into polycarbonates are those teachings in U.S. Pat. No. 4,043,980. Also of interest in this regard is U.S. Pat. No. 3,250,744 which is concerned with polycarbonates based upon in excess of 20 mol % of thiodiphenol (4,4'-dihydroxy-diphenyl sulfide). A disclosure of the incorporation of tetrabromothiodiphenol (3,3',5,5'-tetrabromo-4,4'-dihydroxydiphenyl sulfide) into low molecular weight polycarbonate oligomers appears in Japanese Published Patent Application (Kokai) 67850/75.

In accordance with the present invention a copolymer is provided which has flame retardant characteristics and improved critical thickness values while remaining highly transparent.

BRIEF DESCRIPTION OF THE INVENTION

Polycarbonates are provided having improved critical thickness values and flame retardant characteristics based upon an aromatic diol and a halogenated thiodiphenol represented by the structural formula:

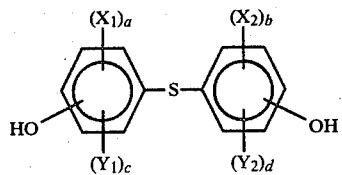

wherein $X_1$ and $X_2$ are halogen and "a"+"b"=1 to 8; $Y_1$ and $Y_2$ are alkyl groups having 1 to 4 carbon atoms; and "c"+"d"=0 to 7. By incorporating an effective amount of the halogenated thiodiphenol based upon the total aromatic diol content into the polymer the critical thickness and flame retardant characteristics of the polycarbonate are substantially improved.

DETAILED DESCRIPTION OF THE INVENTION

When used herein "copolycarbonate resin" means the neat resin with additives; "polycarbonate" means the polycarbonate resin, copolycarbonate resin, or terpolycarbonate resin with additives therein. "Aromatic diol" means an aromatic diol having no halogen therein and primarily having only carbon, hydrogen, sulfur and oxygen atoms. "Aromatic dihydroxy compound" means any or all compounds which are aromatic diols, halogenated aromatic diols or thiodiphenols, or halogenated thiodiphenols.

Copolycarbonate resins of the invention may be prepared by conventional methods of preparation for polycarbonate resins and may have a weight average molecular weight of 10,000 to 200,000 and preferably a melt flow rate of 1 to 24 grams/10 minutes at 300° C. and most preferably a melt flow rate of 1 to 15 grams/10 minutes at 300° C. according to ASTM 1238.

These copolycarbonates differ from the polycarbonate telomers as disclosed in Japanese patent application No. 1973-117745, filed Oct. 2, 1973, entitled "Flame Retardant Resin Composition", in that the copolycarbonate resins of the invention are highly polymeric and form solid articles at room temperature. The referenced Japanese patent application is directed to a low molecular weight composition as a physical additive to thermoplastics to impart flame retardant characteristics.

Any suitable processes, reactants, catalysts, solvents, conditions and the like for the production of the copolycarbonate carbonate resins of this invention which are customarily employed in polycarbonate resin syntheses may be used such as disclosed in German Pat. Nos. 1,046,311 and 962,274; and U.S. Pat. Nos. 3,248,414; 3,153,008; 3,215,668; 3,187,065; 3,028,365; 2,999,846; 2,964,974; 2,970,137; 2,991,273; and 2,999,835 all incorporated herein by reference. The preferred process is the interfacial polycondensation process.

In order to limit the molecular weight one may use monofunctional reactants such as monophenols, for example the propyl-, isopropyl-, and butyl-phenols, especially p-tert. -butyl-phenol and phenol itself. In order to accelerate the reaction, catalysts such as tertiary amines, quaternary ammonium, phosphonium or arsonium salts and the like may be used. The reaction temperature should be about −20° to +150° C., preferably 0° C. to about 100° C.

According to the polycondensation process in a homogeneous phase, the dissolved reaction components are polycondensed in an inert solvent in the presence of an equivalent amount of a tertiary amine base required for absorption of the generated HCl, such as e.g., N,N-dimethyl-aniline, N,N-dimethyl-cyclohexylamine or preferably, pyridine and the like. In still another process, a diaryl carbonate can be transesterified with the aromatic dihydroxy compounds to form the polycarbonate resin.

It is to be understood that it is possible to combine in the processes described above in a chemically meaningful way the aromatic dihydroxy compounds, monohydroxy compounds in the form of the alkali metal salts and/or bis-haloformic acid esters, and the amount of phosgene or carbonyl bromide then still required in order to obtain high molecular products. Other methods of synthesis in forming the polycarbonates of the invention such as disclosed in U.S. Pat. No. 3,912,688 incorporated herein by reference, may be used.

Suitable aromatic diols are for example (4,4'-dihydroxy-diphenyl)-methane; 2,2'-(4,4'-dihydroxy-diphenyl)-propane; 1,1-(4,4'-dihydroxy-diphenyl)-cyclohexane; 1,1-(4,4'-dihydroxy-3,3'-dimethyl-diphenyl)-cyclohexane; 1,1 -(2,2' -dihydroxy-4,4'-dimethyl-diphenyl)butane; 2,2-(2,2'-dihydroxy-4,4'-di-tert.-butyl-diphenyl)-propane or 1,1'-(4,4'-dihydroxy-diphenyl)-1phenyl-ethane; furthermore, methane derivatives which carry besides two hydroxyaryl groups and alkyl residue with at least two carbon atoms and a second alkyl residue with one or more carbon atoms, such as 2,2-(4,4'-dihydroxy-diphenyl)-butane; 2,2-(4,4'-dihydroxy-diphenyl) -pentane; 3,3-(4,4'-dihydroxy-diphenyl)-pentane; 2,2-(4,4'-dihydroxy-dipenyl)-hexane; 3,3-(4,4'-dihydroxy-diphenyl) -hexane; 2,2-(4,4'-dihydroxy-diphenyl)-4-methyl-pentane; 2,2-(4,4'-dihydroxy-diphenyl)-heptane; 4,4-(4,4'-dihydroxy-diphenyl)-heptane (melting point 148-149° C.) or 2,2-(4,4'-dihydroxy-diphenyl)-tri-decane. Suitable di-(monohydroxy-aryl)-alkanes, the two aryl residues of which are different are, for example, 2,2-(4,4'-dihydroxy-3'-methyl-diphenyl)- propane and 2,2-(4,4'-dihydroxy-3-methyl-3'-isopropyl-diphenyl)-butane. Suitable di-(monohydroxyaryl)-alkanes, the alkyl residue of which, linking the two benzene rings, is substituted by an aryl residue are for instance (4,4'-dihydroxy-diphenyl)-phenyl-methane and 1,1-(4,4'-dihydroxy-diphenyl)-1-phenyl-ethane. Examples of aromatic diol wherein the two aryl residues are linked by a sulfur containing group include thiodiphenol and sulfoxide diphenol and sulfonyl diphenol. The use of this first monomer in polycarbonate synthesis is taught in U.S. Pat. No. 3,250,744.

Suitable dihydroxybenzenes and substituted dihydroxy-benzene are hydroquinone, resorcinol, pyrocatecol, methyl hydroquinone and the like. Other suitable dihydroxy-aromatic compounds are 4,4'-dihydroxy-diphenylene; 2,2'-dihydroxy-diphenylene, dihydroxy-naphthalene and dihydroxyanthracene.

The halogenated thiodiphenols useful in the practice of the invention are those represented by the structural formula:

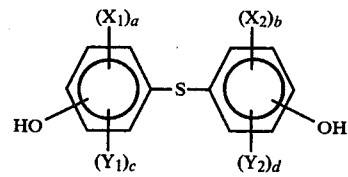

wherein X₁ and X₂ are halogen particularly chlorine, bromine and iodine and most preferably bromine and "a"+"b"=1 to 8; Y₁ and Y₂ are alkyl groups having 1 to 4 carbon atoms; and "c"+"d"=0 to 7. Most preferably the halogenated thiodiphenol is tetrabromo thiodiphenol and is represented by the structural formula:

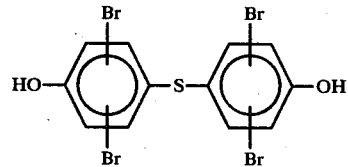

The halogenated thiodiphenols may be synthesized by methods known to those skilled in the art. More particularly the tetrabromo thiodiphenol may be synthesized according to the following reaction:

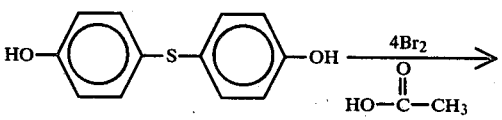

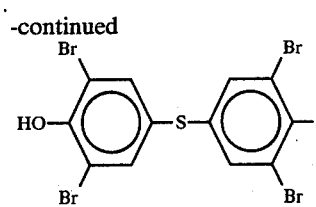

In the alternative, the tetrabromo thiodiphenol may be synthesized by the following reaction procedure:

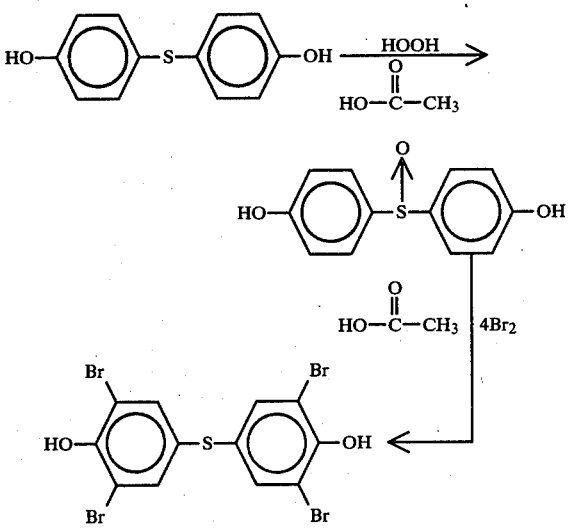

It has been found that the synthesis of the halogenated thiodiphenol using the sulfoxide intermediate yields a higher purity product.

The subject of the present invention is also a process for the production of bis-(4-hydroxy-3,5-dibromophenyl)-sulfide, in which bis-(4-hydroxyphenyl)-sulfide is oxidized with $H_2O_2$ in glacial acetic acid at temperatures of 80° to 90° C. into the bis-(4-hydroxyphenyl)-sulfoxide and those are subsequently reacted with bromine in glacial acetic acid at temperatures of 80° to 90° C. into bis-(4-hydroxy- 3,5-dibromo-phenyl)-sulfide.

The yields of bis-(4-hydroxy-3,5-dibromo-phenyl)-sulfide are 98% of the theory, the product is precipitated at a purity of 99%.

Preferably, the halogenated thiodiphenol is reacted into the copolycarbonate at a level of 2 to 20% by weight based on the total weight as halogenated diphenol and aromatic diol; and more preferably at a level of 2 to 10% by weight. These levels of halogenated thiodiphenol are necessary to achieve the desired critical thickness level and fire retardant characteristics. In reacting the halogenated thiodiphenol it is to be observed that 3 to 10% by weight halogen, and more particularly bromine, either from these halogenated diols alone or from these and other halogenated phenolic diols should be incorporated into the copolymer to impart flame retardant characteristics.

In addition to the halogenated thiodiphenols other non-sulfur containing halogenated phenolic diols may be incorporated in minor amounts into the copolymer and thus form a terpolymer.

The halogenated phenolic diols are any suitable bishydroxyaryl components such as for example the halogen containing bisphenols such as 2,2-(3,5,3', 5'-tetrachloro-4,4'-dihydroxydiphenyl)-propane; 2,2-(3,5,3', 5'-tetrabromo-4,4'-dihydroxydiphenyl)-propane; 2,2-(3,3-dichloro-4,4'-dihydroxydiphenyl)-propan; 2,2-(3,5-dichloro-4,4'-dihydroxy-diphenyl)-propane; 2,2-(3,3'-dichloro-5,5'-dimethyl- 4,4'-dihydroxydiphenyl)-propane; 2,2-(3,3'-dibromo-4,4'- dihydroxydiphenyl)-propane and the like and preferred suitable halogenated phenolic diols are represented by the structural formula:

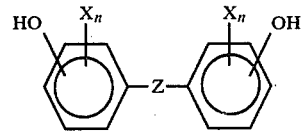

wherein Z is methylene or isopropylidine and X is halogen preferably chlorine or bromine and most preferably bromine and "n" is 1 to 4.

These halogenated diols are incorporated into the polycarbonate at levels sufficient to impart flame retardant characteristics. For example, a halogen content of about 3 to 10% by weight from these monomers and the halogenated thiodiphenol is normally sufficient.

While it is recognized that sulfur containing polycarbonates taught by the prior art produce synergistic flammability characteristics with halogenatd bisphenols (see U.S. Pat. No. 3,912,688), it has not been recognized in the prior art that a halogenated thiodiphenol improves the critical thickness characteristics while maintaining the synergistic flame retardant effects as is provided by the present invention.

The invention will further be illustrated but is not intended to be limited by the following examples.

EXAMPLE Ia 3,5,3',5'-tetrabromo-4,4'-thiodiphenol is prepared as follows.

To a suitable reaction vessel is charged 21.8 grams (0.1 mole) of 4,4'-thiodiphenol and 300 milliliters off acetic acid at room temperature. Sixty-four grams (0.4 mole) of bromine is added to the reaction vessel over the course of an hour and 10 minutes. After the bromine is added the temperature of the reaction mixture is raised to b 65° C. After 10 minutes the product separated at 60° C. and was a blood red color. The reaction slowly started to change to a lighter color and after 35 minutes the solution changed to a light red color. After 15 additional minutes the temperature rose to 75° C. and was held there for 1½ hours. The reaction solution and product were filtered and washed in water. The reaction product had a melting point of 208°–212° C.

EXAMPLE Ib

Production through the 4,4'-bis-(hydroxyphenyl)-sulfoxide.

A mixture of 109 g (0.5 ml) 4,4'thiobisphenol and 150 ml glacial acetic acid are heated to 80° C. until the thiobisphenol is dissolved. Hydrogen peroxide (34 g, 0.5 ml 50% aqueous solution) is added drop by drop within 1½ hours, whereby the temperature is kept constant. After about half of the hydrogen peroxide has been added, the sulfoxide is precipitated. After the complete addition of hydrogen peroxide, the reaction mixture is heated to 90° C., maintained at this temperature for 1½ hours and 200 CC water is added. The precipitated colorless crystals are filtered and washed with water. Yield: 106 g (90% of the theory), melting point 194° C.

The sulfoxide is reacted into bis (3,5-dibromo-4-hydroxyphenyl) sulfide according to the same method bisphenol A. The physical and rheological properties of this polymer are shown on Table 1.

TABLE 1

| Example | Monomer Composition of Copolymer Percent Weight | | | | Critical Thickness (mil) | Izod Impact[5] (notched) | | UL-94 | Burn Test 1/16" | Melt Index of 10 min. |
|---|---|---|---|---|---|---|---|---|---|---|
| | BPA[1] | TBTDP[2] | TBBPA[3] | TDP[4] | | 1/8" | 1/4" | 1/8" | | |
| II | 91 | 9 | — | — | 157 | 14.65 | 1.88 | V-0 | V-0[6] | 6.3 |
| III | 87.45 | | 10.3 | 2.25 | 136 | 14.46 | 2.47 | | V-0 | 3.1 |
| IV | 90 | | 10 | | 130 | 14.53 | 2.2 | | V-2 | 2.9 |

[1]BPA = bisphenol A

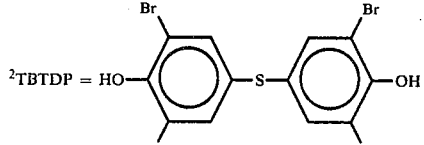

[2]TBTDP =

[3]TBBPA = 3,3',5,5'-tetrabromo bisphenol A

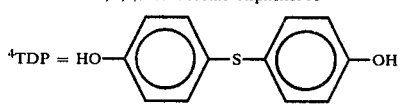

[4]TDP =

[5]Express in ft.-lb./in.
[6]Three out of five test specimens rated V-0, the remaining two specimens rated at up to V-2.

as Ia. The product yield is 98% and its purity 99%, its melting point is 212° to 213° C.

EXAMPLE II

A copolycarbonate resin was prepared by reacting the disodium salts of bisphenol A and 3,3',5,5'-tetrabromo-4,4'-thiodiphenol with phosgene in accordance with the interfacial polycondensation synthesis hereinbefore discussed. It was necessary to meter the tetrabromo-thiodiphenol as a 10% disodium salt solution in water to the reaction cooler overflow since tetrabromo-thiodiphenol was not soluble in commonly used organic solvents used for interfacial polymerization. The weight ratio of bisphenol A to tetrabromo-thiodiphenol was 91:9. The copolycarbonate prepared was tested for physical, mechanical and rheological properties. The test results showed that the polycarbonate had a bromine content of 4.62% and a sulfur content of 0.46%. The heat distortion temperature (ASTM D648) of a sample molded from the copolycarbonate was 142° at 264 psi ASTM. The copolycarbonate had a melt stability at 300° C. as follows:

| 5 minutes | Melt viscosity | Pa.s | 600 |
|---|---|---|---|
| 35 minutes | Melt viscosity | Pa.s | 545 |
| 65 minutes | Melt viscosity | Pa.s | 540 |

Upon molding at 550° F. the polycarbonate has a percent brightness of 87.55 and at molding at 650° F. had a brightness of 81.72%. Other physical nd rheological properties are reported on Table 1.

EXAMPLE III

A terpolycarbonate was prepared from the reaction product of 87.45 weight % bisphenol A; and 10.3 weight % tetrabromo bisphenol A; and 2.25 weight % thiodiphenol in accordance with U.S. Pat. No. 4,043,980. The test results of this polymer are shown on Table 1.

EXAMPLE IV

A copolycarbonate was prepared from 90 parts by weight bisphenol A and 10 parts by weight tetrabromo bisphenol A. The physical and rheological properties of this polymer are shown on Table 1.

As is shown in Table 1 polycarbonates prepred from the halogenated thiodiphenol show high critical thickness values in comparison to polymers having the tetrabromo bisphenol A and the polymers which include thiodiphenol and tetrabromo bisphenol A. Further, the melt index of the polymers of the invention is high as compared with the other examples shown. The higher melt index provides easier molding procedures. Further, the flame retardant characteristics of the polymer in Example II, which is in accordance with the invention, have a V-0 rating at 1/16" according to the UL-94 burn test. The UL-94 test was conducted as follows:

Test specimens of polycarbonate are molded in bars having dimensions of 1.27 mm × 12.7 mm × 1.6 mm. The panels are mounted vertically so that the bottom of the test specimen is 305 mm above a swatch of surgical cloth. Each test bar is individually ignited for two successive ten-second ignitions and the burning characteristics after each ignition are noted and the sample is rated. A Bunsen burner is used to ignite the sample with a three quarter inch (10 mm) blue flame from natural gas having approximately 1,000 BTU per cubic foot heat content.

The UL-94 V-0 classification exemplifies the following properties in materials tested in accordance with the UL-94 specification. Polycarbonates within this class have no samples which burn for more than ten seconds after each application of the test flame; do not have a total flaming time of more than 50 seconds for the two flame applications of each set of samples; do not have any specimens which burn completely up to the holding clamp which is positioned at the top of the specimen; do not have any specimens which ignite the cotton which is placed below the sample with flaming drips or particles; and do not have any specimens which glow longer than 30 seconds after removal of the test flame.

Other UL-94 classifications exemplify samples which are less flame retardant and self-extinguishing, and which have flaming drips or particles. These classifications are UL-94 V-1 and V-2. The polycarbonates within the scope of the present invention characteristically demonstrate those properties in the UL-94 V-0 classification.

Thus, in accordance with the invention polymers based upon an aromatic diphenol and a halogenated thiodiphenol exhibit high critical thickness properties and excellent flame retardant characteristics.

Although the invention has been described with reference to specific materials and testing procedures, the invention is only to be limited insofar as is set forth in the accompanying claims.

What is claimed is:

1. In a thermoplastic polycarbonate based upon the reaction product of a halogen-free aromatic diol selected from the group consisting of
   (i) dihydroxy diphenyl alkanes,
   (ii) dihydroxy benzenes,
   (iii) aromatic diols wherein the two aryl residues are linked by a sulfur-containing group, and
   (iv) dihydroxy diphenyls and a carbonic acid derivative, the improvement comprising:
a sufficient amount of a halogenated thiodiphenol co-reacted in said reaction product to impart flame retardant characteristics to said polycarbonate, said halogenated thiodiphenol being represented by the structural formula:

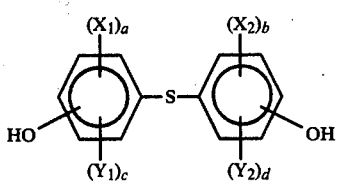

wherein $X_1$ and $X_2$ are halogen and $Y_1$ and $Y_2$ are alkyl radicals having 1 to 4 carbon atoms; and wherein a, b, c and d independently are integers from 0 to 4 with the proviso that the sum of said a and said b is from 1 to 8 and that the sum of said c and said d is from 0 to 7.

2. The polycarbonate of claim 1 wherein said halogenated thiodiphenol is represented by the structural formula:

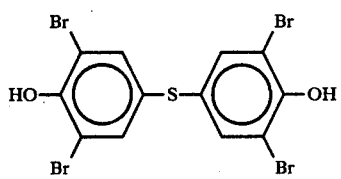

3. The polycarbonate of claim 1 wherein said halogenated thiodiphenol is co-reacted in said reaction product at a level of 2 to 20% by weight based on the total weight of said halogenated thiodiphenol and said aromatic diol.

4. The polycarbonate of claim 1 wherein said halogenated thiodiphenol is co-reacted in said reaction product at a level of 2 to 10% by weight based on the total weight of said halogenated thiodiphenol and said aromatic diol.

5. A flame retardant thermoplastic polycarbonate comprising the reaction product of:
(a) a halogen-free aromatic diol selected from the group consisting of
   (i) dihydroxy diphenyl alkanes,
   (ii) dihydroxy benzenes,
   (iii) aromatic diols wherein the two aryl residues are linked by a sulfur-containing group and
   (iv) dihydroxy diphenyls; and
(b) a halogenated thiodiphenol represented by the structural formula:

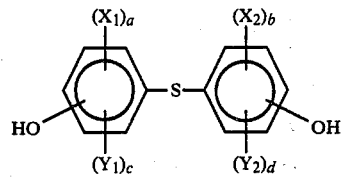

wherein $X_1$ and $X_2$ are halogen and $Y_1$ and $Y_2$ are alkyl radicals having 1 to 4 carbon atoms; and wherein a, b, c and d independently are integers from 0 to 4 with the proviso that the sum of said a and said b is from 1 to 8 and that the sum of said c and said d is from 0 to 7; and
(c) a member selected from the group consisting of carbonyl bromide, phosgene, bischloroformic esters of (a) and (b) and diaryl carbonates, wherein (b) is present in a sufficient amount to provide 3 to 10% by weight halogen in said thermoplastic polycarbonate.

6. The polycarbonate of claim 5 wherein (b) is reacted at a level of 2 to 20% by weight based on the total weight of (a) and (b).

7. The polycarbonate of claim 5 wherein (b) is reacted at a level of 2 to 10% by weight based on the total weight of (a) and (b).

8. The polycarbonate of claim 5 wherein (b) is represented by the structural formula:

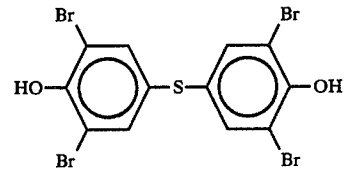

9. The polycarbonate of claim 5 wherein said aromatic diol is bisphenol A.

10. A flame retardant thermoplastic polycarbonate having a melt flow rate of 1 to 24 grams per 10 minutes at 300° C. according to ASTM 1238 comprising a terpolycarbonate resin which is the reaction product of
(a) a halogen-free aromatic diol selected from the group consisting of
   (i) dihydroxy diphenyl alkanes,
   (ii) dihydroxy benzenes,
   (iii) aromatic diols wherein the two aryl residues are linked by a sulfur-containing group and
   (iv) dihydroxy diphenyl; and
(b) about 2 to 20% by weight of a halogenated thiodiphenol represented by the structural formula

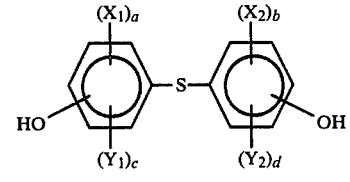

wherein $X_1$ and $X_2$ are halogen and $Y_1$ and $Y_2$ are alkyl radicals having 1 to 4 carbon atoms; and wherein a, b, c and d independently are integers from 0 to 4 with the proviso that the sum of said a and said b is from 1 to 8 and that the sum of said c and said d is from 0 to 7; and
(c) a halogenated sulfur-free phenolic diol; and
(d) a member selected from the group consisting of carbonyl bromide, phosgene, bischloroformic esters of (a), (b) and (c) and diaryl carbonates, said reaction product incorporating a sufficient amount of (b) and (c) to provide the reaction product with a halogen content between about 3 and 10% by weight.

11. In a thermoplastic polycarbonate based upon the reaction product of a halogen-free aromatic diol selected from a group consisting of
  (i) dihydroxy diphenyl alkanes,
  (ii) dihydroxy benzenes and
  (iii) dihydroxy diphenyls and a carbonic acid derivative, the improvement comprising co-reacting in said reaction products 2 to 20%, relative to the weight of said reaction product, of a halogenated thiodiphenol of the structural formula:

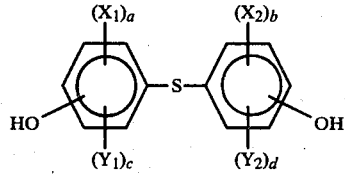

wherein $X_1$ and $X_2$ are halogen and $Y_1$ and $Y_2$ are alkyl radicals having 1 to 4 carbon atoms; and wherein a, b, c and d independently are integers from 0 to 4 with the proviso that the sum of said a and said b is from 1 to 8 and that the sum of said c and said d is from 0 to 7.

* * * * *